US00PP14558P29

(12) United States Plant Patent
Kievit

(10) Patent No.: US PP14,558 P2
(45) Date of Patent: Feb. 24, 2004

(54) CALIBRACHOA PLANT NAMED 'KIECABUL'

(50) Latin Name: *Calibrachoa procumbens*
Varietal Denomination: Kiecabul

(75) Inventor: Christa Kievit, Venhuizen (NL)

(73) Assignee: Kieft Seeds Holland, Venhuizen (NL)

( * ) Notice: Subject to any disclaimer, the term of this patent is extended or adjusted under 35 U.S.C. 154(b) by 33 days.

(21) Appl. No.: 10/162,989

(22) Filed: Jun. 5, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H Para
(74) *Attorney, Agent, or Firm*—C. A. Whealy

(57) ABSTRACT

A distinct cultivar of Calibrachoa plant named 'Kiecabul', characterized by its uniform, low-growing, cascading and outwardly spreading plant habit; freely and continuous branching habit; small leaves; and freely flowering habit, numerous violet-colored flowers.

1 Drawing Sheet

Botanical classification/cultivar designation: *Calibrachoa procumbens* cultivar Kiecabul.

BACKGROUND OF THE INVENTION

The present Invention relates to a new and distinct cultivar of Calibrachoa plant, botanically known as *Calibrachoa procumbens*, and hereinafter referred to by the cultivar name Kiecabul.

The new Calibrachoa is a product of a planned breeding program conducted by the Inventor in Venhuizen, The Netherlands. The objective of the breeding program is to create new Calibrachoas with numerous flowers with attractive flower colors.

The new Calibrachoa originated from a cross made by the Inventor during the summer of 1999 of a proprietary Calibrachoa selection identified as KA-1796, not patented, as the female, or seed parent, with a proprietary Calibrachoa selection identified as KA-12-1777, not patented, as the male, or pollen parent. The new Calibrachoa was selected as a single flowering plant from the resulting progeny by the Inventor in 1999 in Venhuizen, The Netherlands.

Asexual reproduction of the new cultivar by terminal cuttings taken in Venhuizen, The Netherlands since 1999 has shown that the unique features of this new Calibrachoa are stable and reproduced true to type in successive generations.

SUMMARY OF THE INVENTION

Plants of the cultivar Kiecabul have not been observed under all possible environmental conditions. The phenotype may vary somewhat with variations in environment such as temperature and light intensity without, however, any variance in genotype.

The following traits have been repeatedly observed and are determined to be the unique characteristics of 'Kiecabul'. These characteristics in combination distinguish 'Kiecabul' as a new and distinct cultivar:

1. Uniform, low-growing, cascading and outwardly spreading plant habit.
2. Freely and continuous branching habit; short internodes; dense and bushy plant growth habit.
3. Small leaves.

4. Freely flowering habit, numerous violet-colored flowers.

Plants of the new Calibrachoa differ from the female parent, the selection KA-1796, in plant growth habit and flower color as plants of the female parent are not as trailing and have lighter violet-colored flowers. Plants of the new Calibrachoa differ from the male parent, the selection KA-12-1777, primarily in flower color as plants of the male parent have darker violet-colored flowers with distinct venation.

Plants of the new Calibrachoa can be compared to plants of the Calibrachoa cultivar Carillon Blue, not patented. In side-by-side comparisons conducted in Venhuizen, The Netherlands, plants of the new Calibrachoa differed from plants of the cultivar Carillon Blue in the following characteristics:

1. Plants of the new Calibrachoa flowered earlier than plants of the cultivar Carillon Blue.
2. Plants of the new Calibrachoa had darker violet-colored flowers than plants of the cultivar Carillon Blue.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Calibrachoa.

The photograph at the top of the sheet comprises a side perspective view of a typical flowering plant of 'Kiecabul' grown in a container.

The photograph at the bottom of the sheet comprises a close-up view of typical developing flower buds and flowers, lower surface of an opened flower, and upper and lower of typical leaves of 'Kiecabul'.

DETAILED BOTANICAL DESCRIPTION

The aforementioned photographs and following observations and measurements describe plants grown in Lompoc, Calif., under commercial practice during the winter and spring in a polycarbonate-covered greenhouse with day temperatures about 18 to 24° C., night temperatures about 16 to 18° C., and light levels about 4,000 to 8,000 foot-candles. One cutting was planted per 15-cm container and plants were grown for about 12 weeks. In the following description, color references are made to The Royal Horticultural Society Colour Chart, 1995 Edition, except where general terms of ordinary dictionary significance are used.

Botanical classification: *Calibrachoa procumbens* cultivar Kiecabul.

Parentage:

*Female parent.*—Proprietary *Calibrachoa procumbens* selection identified as KA-1796, not patented.

*Male parent.*—Proprietary *Calibrachoa procumbens* selection identified as KA-12-1777, not patented.

Propagation:

*Type cutting.*—Terminal vegetative cuttings.

*Time to initiate roots, summer and winter.*—About 10 days at 20° C.

*Time to develop roots.*—Summer: About 28 days at 20° C. Winter: About 32 days at 20° C.

*Root description.*—Fine, fibrous, white.

*Rooting habit.*—Freely branching, moderately dense.

Plant description:

*Form.*—Annual flowering plant; uniform, low-growing, cascading and outwardly spreading plant habit; plants eventually becoming hemispherical to spherical in shape. Freely and continuously branching habit with about 14 main lateral branches per plant with lateral branches forming potentially at every node; short internodes; dense and bushy plant growth habit. Moderately vigorous.

*Usage.*—Appropriate for hanging baskets, window boxes, patio containers and landscape applications.

*Plant height.*—About 7 cm.

*Plant diameter.*—About 37 cm.

*Lateral branches.*—Length: About 26 cm. Diameter: About 2 mm. Internode length: About 1.5 cm. Texture: Pubescent; viscid. Color: 144B.

*Foliage description.*—Arrangement: Before flowering, alternate; after flowering, opposite; simple. Length: About 2.2 cm. Width: About 8 mm. Shape: Narrowly elliptic to narrowly oblong. Apex: Rounded. Base: Attenuate. Margin: Entire. Texture, upper surface: Slightly pubescent; viscid. Texture, lower surface: Glabrous; viscid. Venation pattern: Pinnate, arcuate. Color: Young foliage, upper and lower surfaces: 147A. Mature foliage, upper surface: 147A. Mature foliage, lower surface: 147B. Venation, upper and lower surfaces: 147B. Petiole length: About 5 mm. Petiole diameter: About 1 mm. Petiole color: 147B.

Flower description:

*Flower type and habit.*—Salverform flowers; single, axillary. Flowers face mostly upward or outward and are held above the foliage. Flowers persistent.

*Quantity of flowers.*—Very freely flowering, typically about 250 open flowers and flower buds per plant.

*Natural flowering season.*—Long day responsive; spring until frost in the autumn; flowering continuous during the flowering period.

*Flower longevity on the plant.*—About three to four days in the landscape.

*Fragrance.*—None detected.

*Flower diameter.*—About 3 cm.

*Flower depth (height).*—About 2.7 cm.

*Flowering buds (showing color).*—Length: About 2 cm. Diameter: Apex, about 5 mm; base, about 3 mm. Shape: Elongated oblong. Color: 85A.

*Corolla.*—Arrangement/appearance: Single whorl of five petals, fused into flared trumpet with distinct clefts between petal lobes. Petal length from throat: About 1.3 cm. Petal width: About 1.5 cm. Petal shape: Roughly spatulate or fan-shaped. Petal apex: Rounded and slightly emarginate. Petal margin: Entire. Petal texture: Smooth, satiny. Color: Petal, upper surface, when opening: Brighter than 83B. Petal, lower surface, when opening: 85B to 85C. Petal, upper surface, fully opened: 88A; color fading to 88B to 88C with subsequent development. Petal, lower surface, fully opened: 88D. Flower throat (inside): Towards apex, 157A; towards base, 150B. Flower tube (outside): 157A. Venation, upper and lower petal surfaces: Same as petal color. Venation, throat and tube: 79C.

*Sepals.*—Arrangement/appearance: Single whorl of five sepals fused at base, star-shaped. Length: About 1.3 cm. Width: About 3 mm. Shape: Strap-like, narrowly elliptic. Apex: Acute. Margin: Entire. Texture, upper and lower surfaces: Pubescent. Color, upper surface: 147A. Color, lower surface: 147A to 147B.

*Peduncles.*—Length: About 1.4 cm. Width: About 1 mm. Angle: About 45° to the stem. Strength: Moderately strong; wiry. Texture: Pubescent. Color: 144C.

*Reproductive organs.*—Stamens: Quantity/arrangement: Five. Anther shape: Ovoid. Anther length: Less than 1 mm. Anther color: 10A. Pollen amount: Scarce. Pollen color: 10A. Pistils: Quantity: One. Pistil length: About 1 cm. Stigma shape: Anvil-shaped. Stigma color: 144C. Style length: About 7 mm. Style color: 144C to 144D. Ovary color: 150C.

*Seed/fruit.*—Seed and fruit production has not been observed.

Disease/pest resistance: Plants of the new Calibrachoa have not been noted to be resistant to pathogens or pests common to Calibrachoa.

It is claimed:

1. A new and distinct cultivar of Calibrachoa plant named 'Kiecabul', as illustrated and described.

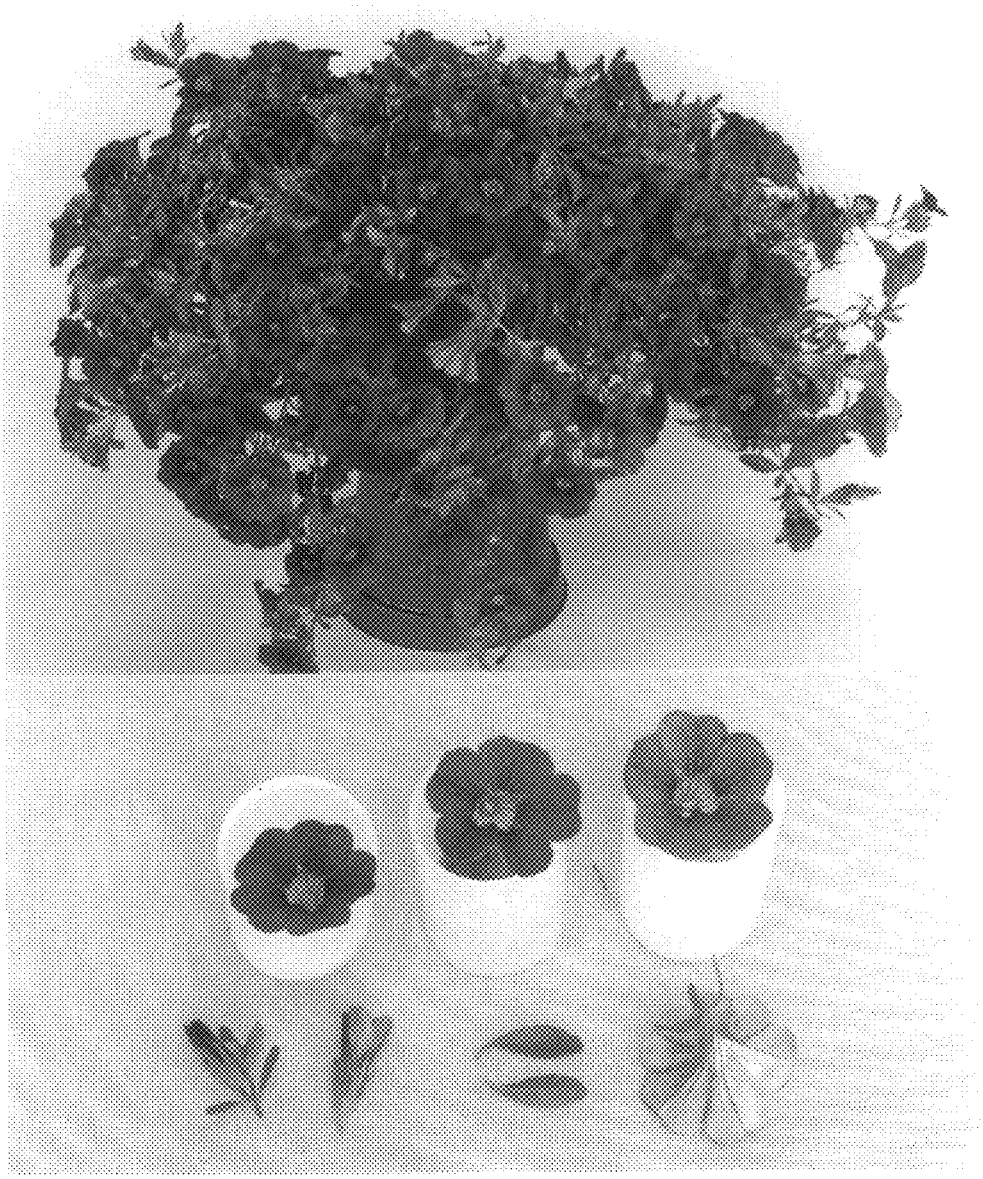

* * * * *